United States Patent
Velozo et al.

(10) Patent No.: US 12,209,264 B2
(45) Date of Patent: Jan. 28, 2025

(54) ANTHOCYANIN PRODUCTION PROCESS FROM ARISTOTELIA CHILENSIS CALLUS CULTURES

(71) Applicants: UNIVERSIDAD MAYOR, Santiago (CL); FUNDACION COPEC UNIVERSIDAD CATÓLICA, Santiago (CL)

(72) Inventors: Juan Velozo, Santiago (CL); Steffany Huth, Santiago (CL); Victor Polanco, Santiago (CL)

(73) Assignees: Universidad Mayor, Santiago (CL); Fundacion Copec Universidad Católica, Santiago (CL)

( * ) Notice: Subject to any disclaimer, the term of this patent is extended or adjusted under 35 U.S.C. 154(b) by 15 days.

(21) Appl. No.: 17/757,921

(22) PCT Filed: Dec. 23, 2019

(86) PCT No.: PCT/CL2019/050150
§ 371 (c)(1),
(2) Date: Jun. 23, 2022

(87) PCT Pub. No.: WO2021/127792
PCT Pub. Date: Jul. 1, 2021

(65) Prior Publication Data
US 2023/0060009 A1 Feb. 23, 2023

(51) Int. Cl.
*C12P 17/06* (2006.01)
*A23L 5/43* (2016.01)
*A23L 33/105* (2016.01)
*C12N 5/00* (2006.01)
*C12N 5/04* (2006.01)

(52) U.S. Cl.
CPC .............. *C12P 17/06* (2013.01); *A23L 5/43* (2016.08); *A23L 33/105* (2016.08); *C12N 5/0025* (2013.01); *C12N 5/04* (2013.01); *A23V 2002/00* (2013.01); *C12N 2500/24* (2013.01); *C12N 2500/34* (2013.01); *C12N 2500/76* (2013.01)

(58) Field of Classification Search
CPC ............................ A23L 33/105; C12N 5/0025
See application file for complete search history.

(56) References Cited

FOREIGN PATENT DOCUMENTS

CN 107721545 2/2018

OTHER PUBLICATIONS

Pamela Andrea Diaz Abarca, Production of anthocyanins from Aristotelia Chilensis in bioreactors for nutraceutical use, 2014, Repositorio academico de la universidad de chile, (Year: 2014).*
A. Decendit, Condensed tannin and anthocyanin production in Vitis vinifera cell suspension cultures, 1996, Plant cell reports 15:762-765, (Year: 1996).*
Maria Constance Sadino Riquelme, "invitro culture and induction strategies of *Aristotelia chilensis* (Maqui) for obtaining anthocyanins", 2015, Repositorio academico de la universidad de chile (Year: 2015).*
Pamela Andrea Diaz Abarca, "Production of anthocyanins from Aristotellia Chilensis in bioreactors for nutraceutical use", 2014, Repositorio academico de la universidad de chile (Year: 2014).*
International Search Report issued in International Application No. PCT/CL2019/050150, Aug. 10, 2020, 10 pages w/translation.
Saw, et al., "Effect of Elicitors and Precursors on the Synthesis of Anthocyanin in Grape *Vitis vinifera* Cell Cultures", Energy Research Journal 1 (2): 189-192, 2010.
Saw, et al., "Stimulation of anthocyanin synthesis in grape (*Vitis vinifera*) cell cultures by pulsed electric fields and ethephon", Plant Cell Tiss Organ Cult (2012) 108:47-54.
Cespedes, et al, "In Vitro Culture of Aristoteli Chilensis (Mol.) Stuntz Elaeocarpaceae", Gayana Bot. 52(2): 77-82, 1995—Abstract.
Biswas, et al., "Plant Anthocyanins: Biosynthesis, Bioactivity and in vitro Production from tissue cultures", Advances in Biotechnology & Microbiology, vol. 5, No. 5, Aug. 2017, pp. 00118-00124.

* cited by examiner

*Primary Examiner* — Charles Logsdon
*Assistant Examiner* — Zachariah Allan Kay
(74) *Attorney, Agent, or Firm* — HSML P.C.

(57) ABSTRACT

The invention points to a process of production of anthocyanins from *Aristotelia chilensis* callus cultures, which is divided into 2 essential steps: the first is the obtaining of biomass in an *A. chilensis* callus culture, the second step consists of eliciting the production of anthocyanins in the culture, to obtain the desired product. In this way, callus cultivation is presented as a new alternative to provide a nutritional additive rich in anthocyanins appropriate for the food industry, or any other application that requires anthocyanins that does not depend on seasonality or environmental factors.

7 Claims, 1 Drawing Sheet

ANTHOCYANIN PRODUCTION PROCESS FROM ARISTOTELIA CHILENSIS CALLUS CULTURES

TECHNICAL FIELD

The invention relates to a process of production of anthocyanins, especially for the food and nutraceutical industries, from callus cultures of *Aristotelia chilensis*.

BACKGROUND OF THE INVENTION

In the food industry, specifically in the area of dyes, there is currently a strong demand focused on natural colorants, because most artificial colors have some level of toxicity. That is why anthocyanins, being a vegetable pigment, enters as a strong competitor in the colorant industry, thus being able to displace its synthetic variant.

Maqui (*Aristotelia chilensis*) in addition to having a high concentration of anthocyanins, is characterized by its anti-inflammatory, anticancer, antibacterial and neuroprotective properties, among others, which makes it useful as a functional food and required as a raw material in the nutraceutical and cosmetic industry.

The current demand for Maqui fruit either for beverages or foods that contain it, or as a source of anthocyanins for the industry that uses it as a natural nutraceutical dye, is not fully supplied. The lack of crops and the seasonality of the fruit make for a deficit in the amount of raw material that is available for the market. In addition, the currently available crops are subject to the variability in the quality of the fruit, either through the genetic variation of the specimens or through the environmental and harvesting conditions. The collection of fruit is manual and occurs in geographical areas with different characteristics, which makes it difficult to have a standard of quality of the raw material. In Chile, approximately 170 tons of maqui are collected per year, which is far from the 600-800 tons/year that are forecast as demand for 2020.

In order to solve this technical problem, the inventors have developed a production plan for a concentrate of anthocyanins obtained from Maqui cell cultures, which makes it possible to decouple the supply of these compounds from the seasonality of the fruit and the elaboration of a product of standardized quality. The process of the invention for the production of anthocyanins consists of obtaining the biomass of *Aristotelia chilensis* in callus culture and its subsequent eliciting of anthocyanins, in this way a product rich in these compounds is obtained, non-seasonally, and of constant quality, since it is produced in a controlled environment.

In the state of the art, we have not found publications that obtain anthocyanins from *A. chilensis* callus cultures. Among the nearby papers are the publication of Saw, N. et al ("Effect of elicitors and precursors on the synthesis of anthocyanin in grape *Vitis vinifera* cell cultures." Energy Res J 1.2 (2010): 189-191), where the production of anthocyanins in cell cultures of vines is studied. In addition to the obvious difference of plant material, the document analyzes the effect of ethephon and other compounds on the production of anthocyanins in cell cultures of *Vitis vinifera*, and it is seen that ethephone, a key compound in the process of the invention negatively affects, with results inferior to the control, both the production of the biomass and also in the production of anthocyanins in that model.

Among the closest patent documents is the Chinese patent application CN107721545 A (UNIV FOSHAN, 2018-02-23). This patent application discloses a method based on the control of the proportions of potassium nitrate as a source of nitrogen, to promote the accumulation of anthocyanins in callus cultures. A culture medium of general use is shown, although it is indicated that it serves in celosia calluses. The medium is characterized by the content of nutrients selected to promote the accumulation of anthocyanins, but the invention differs from this document in that it comprises a stage of induction or eliciting during cultivation, which is not suggested in document CN107721545 A.

Surprisingly, the inventors have managed to obtain a callus culture of *Aristotela chilensis* that, despite being obtained from cotyledons and leaves of the plant, manages to express and produce the anthocyanins of the maqui fruit. In this way, the cultivation of calluses is presented as a new alternative to provide a nutritional additive rich in anthocyanins appropriate for the food industry, or any other application that requires anthocyanins.

DETAILED DESCRIPTION OF THE INVENTION

Figure 1:
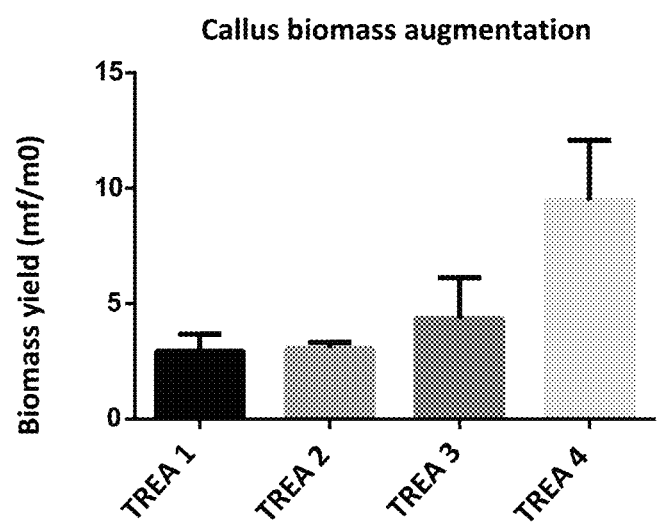
FIG. 1. Biomass yield graph (mf/m0) of calluses subjected to biomass augmentation treatment, the ratio between the final biomass (mf) and initial biomass (m0) is shown.

The invention points to a process of production of anthocyanins from callus cultures of *Aristotelia chilensis*.

This process, of anthocyanin production, is divided into 2 essential stages. The first is the obtaining of biomass in the cultivation of calluses of *A. chilensis*, the second stage consists of the eliciting of the production of anthocyanins in the culture, to obtain the desired product.

Essentially, the production of anthocyanins from *Aristotelia chilensis* callus cultures comprises the following steps:
  (a) growing calluses of *Aristotela chilensis* in a vegetable culture medium supplemented with sugars, also containing between 0.1 to 2 mg/L of BAP (6-Benzyl amino purine), between 0.1 to 2 mg/L of NAA (naphthaleneacetic acid) and between 100 to 500 mg/L ascorbic acid; for a period of between 5 and 50 days; with alternating light and dark;
  (b) eliciting anthocyanin production by maintaining stage (a) culture in a vegetable growing medium supplemented with sugars and between 10 to 500 mg/L ethephon; for a period of between 5 and 30 days, with alternating light and dark.

In step a) of the process the sugars in the medium are in a total concentration of between 1 to 5% w/v and are chosen between sucrose, glucose and/or fructose and the medium optionally comprises between 20 to 200 mg/L of iron chelate. And the culture is kept in a photoperiod of between 12 to 20 light hours and between 12 to 4 hours of darkness a day, with a light intensity of between 5,000 to 30,000 lux.

In step b) of the process the sugars in the medium are in a total concentration of between 1 to 20% w/v and are chosen between sucrose, glucose and/or fructose and the medium optionally comprises between 20 to 200 mg/L of iron chelate; and between 10 to 500 mg/L ethephon; for a period of between 5 and 30 days. And the culture is kept in a photoperiod of between 12 to 20 light hours and between 12 to 4 hours of darkness a day, with a light intensity of between 5,000 to 20,000 lux. Iron chelate can be iron sulfate, hydrated mono, penta or hepta.

Where, additionally at the end of step b) the anthocyanins are extracted from the calluses in culture. Or alternatively at the end of step b) the *A. chilensis* calluses are dried, for example, by freeze-drying and ground until a powder rich in anthocyanins is obtained.

In a preferred embodiment the powder obtained can be used directly as a supplement for food and beverages, and also as a source of anthocyanins for nutraceutical products.

As indicated, the purpose of step a) of the method of the invention is to obtain biomass in large quantities, the inventors have carried out studies on a laboratory scale, where they have managed to obtain a biomass yield of the calluses of *A. chilensis* of up to 9.5 times the initial biomass, in 21 days of cultivation.

The second step of the process of invention consists of the eliciting of the production of anthocyanins in cultures. At this stage, the calluses of *A. chilensis* in culture are subjected to nutritional stress, so that the metabolic pathway of anthocyanin production is activated and thus achieves the change of coloration of the calluses from green to purple, the characteristic color for the presence of anthocyanins in the plant tissue.

After step a) of biomass increase, the culture medium is removed and the calluses are kept in vegetable culture medium, supplemented with sugars, and as an elicitor of ethephon. Growing conditions are photoperiod 16 hours light 8 hours darkness, constant agitation of 100 rpm. In these conditions it is possible to obtain completely colored calluses with a high content of anthocyanins.

Optionally, colored calluses can be processed to obtain an extract of anthocyanins in powder format. To do this, in a preferred embodiment the calluses are subjected to centrifuge for 15 minutes, to remove the excess culture medium. Then they are freeze-dried for 72 hrs. and then they go to grinding in a knife grinder for 10 minutes. At the end of the process, a quality control of the product is carried out, where the anthocyanin content will be measured.

The product of the invention has the advantage that it is not under the effect of the seasonality of the fruit, since the raw material of the production of anthocyanins is present throughout the year for the case of the invention. It should also be noted that the variability of the fruits, both by genetic variables of the plants or by environmental climatic variables, does not affect the production of anthocyanin in our case, because the production of this is regulated by other factors that make us independent of genetic variability. The process of the invention allows for obtaining a biomass with high content of anthocyanins, which could compete with the biomass of fruit obtained in a season.

Below are some examples, which show preferred embodiments of the invention. Within the examples there are conditions that give better results than the others tested, however, all options are considered part of the invention. These examples should be considered as illustrative and not limiting the scope of the invention process.

Examples

The process of obtaining anthocyanins is divided into the increase of the biomass of calluses through the addition of nutrients and hormones, followed by the eliciting of the production of anthocyanins with the help of elicitors.

Example 1: Increase in Callus Biomass

For the increase of biomass, calluses of *A. chilensis* obtained by traditional methods of callogenesis are provided. These calluses were grown in 4 different treatments or media which are specified in Table 1.

The culture conditions were photoperiod 16 light hours with light intensity of 27,000 lux and 8 hours of darkness, for 28 days.

FIG. 1 shows the comparison of the results obtained with each treatment used, where after the process it was possible to obtain a yield of 9.5 times increase in initial biomass with treatment N° 4, this means that for 1 g of inoculated fresh callus 9.5 g of fresh callus is obtained at the end of the process. In the case of treatment N° 1 and N° 2 the biomass was tripled or and for the treatment N° 3 the biomass was quintupled.

TABLE 1

| Description of treatment used for biomass augmentation | | | |
| --- | --- | --- | --- |
| Treatment No 1 | Treatment No 2 | Treatment No 3 | Treatment No 4 |
| Medio Murashige & Skoog | Medio Murashige & Skoog | Medium Murashige & Skoog modified | Modified Gamborg B5 medium |
| 2% w/v sucrose | 2% w/v sucrose | 2% (sucrose, glucose and fructose) | 2% (sucrose, glucose and fructose) |
| 0.5 mg/L BAP | 0.5 mg/L BAP | 0.5 mg/L BAP | 0.5 mg/L BAP |
| 1 mg/L NAA | 1 mg/L NAA | 1 mg/L NAA | 1 mg/L NAA |
| | 83.4 mg/L Iron chelate (EDTA) | | |

Example 2: Anthocyanin Elicitation

After the process of increasing cellular biomass, calluses obtained according to treatment 4 described in example 1, were transferred to treatments or means of eliciting the production of anthocyanins, which are specified in Table 2.

TABLE 2

| Description of treatments used for eliciting. | | |
| --- | --- | --- |
| Treatment No 1 | Treatment No 2 | Treatment No 3 |
| Murashige & Skoog medium without nitrogen | Murashige & Skoog medium without nitrogen | Modified Gamborg B5 medium |
| 2% sucrose | 10% sucrose | 2% (sucrose, glucose and fructose) |
| 100 mg/L ethephon | 100 mg/L ethephon | 100 mg/L ethephon |

The growing conditions were photoperiod 16 hours red light with light intensity of 11,000 lux and 8 hours of darkness, for 14 days.

After 14 days the calluses were harvested and subjected to a process of extraction and quantification of anthocyanins. The calluses were weighed and part of them transferred to Falcon Tubes to quantify and isolate the anthocyanins produced. For this, 5 ml of acidified methanol (0.1% HCl) was added to the Falcon tubes and left stirring at 200 rpm for 1 hour. The mixture was centrifuged at 10,000 g for 15 minutes, the supernatant was recovered and stored at 4° C.

3 ml of acidified methanol was added to the remaining pellet and again left stirring for an hour, centrifuged and the supernatant was joined with the previous one. The concentration of anthocyanins in the extracts was quantified through the differential pH method.

From treatment 1, a callus with reddish colored areas was obtained, the quantification showed that the callus had an average concentration of 2.2 mg eq del/pgd of anthocyanins.

In the case of treatment 2, a reddish colored callus was obtained and with purple areas, the quantification showed that the callus had an average concentration of 3.8 mg eq del/pgd.

Figure 2:
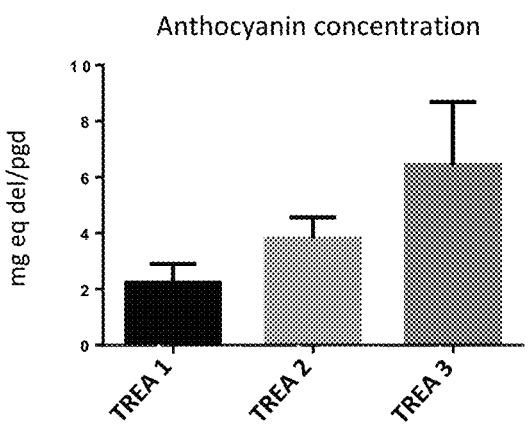
FIG. 2. Graph of anthocyanin concentration expressed in milligrams equivalent of delphinidine per gram of dry weight (mg eq del/pgd) of calluses subjected to an elicitation treatment for the production of anthocyanins.

Finally, for treatment 3 a purple-colored callus was obtained, the quantification showed that the callus had an average concentration of 6.4 mg eq del/pgd of anthocyanins, the results are graphed in FIG. 2.

The rest of the biomass obtained was freeze-dried for 72 hrs at a temperature of −70° C. and pressure of 0.0007 pascal and a purple dry powder, rich in anthocyanins, was obtained.

The powder obtained can be mixed with food or beverages providing nutraceutical anthocyanins. Or it can be used as a source of anthocyanins in any composition that requires them.

The preceding examples demonstrate the effectiveness of the invention process. For the expert in the technique, modifications to these achievements will be evident, which would have similar results to those described, leaving all these modifications included in the scope of the invention, as indicated in the attached claims.

The invention claimed is:

1. A process of production of anthocyanins from *Aristotelia chilensis* callus cultures comprising:

(a) growing *Aristotela chilensis* callus in a vegetable culture medium supplemented with a mix of sugars in a total concentration of between 1 to 5% w/v, wherein the mix of sugars includes sucrose, glucose, and fructose, also containing between 0.1 and 2 mg/L of BAP (6-Benzyl amino purine) and between 0.1 to 2 mg/L of NAA (naphthaleneacetic acid); for a period of between 5 and 50 days, with alternating light and darkness; and b) eliciting the production of the anthocyanins by maintaining the culture of the step a) in a growing medium for vegetables, supplemented with the sugars, and ethephone between 10 to 500 mg/L; for a period of between 5 and 30 days, with alternating light and darkness.

2. The process according to claim 1, wherein in the step a), the vegetable culture medium comprises between 20 to 200 mg/L of iron chelate.

3. The process according to claim 1, wherein in the step a), the *Aristotela chilensis* callus is maintained in a photoperiod of between 12 to 20 light hours and between 12 to 4 hours of the darkness per day, with a light intensity of between 5,000 to 30,000 lux.

4. The process according to claim 1, wherein in the step b), the vegetable culture medium comprises between 20 to 200 mg/L of chelate of hierro.

5. The process according to claim 1, wherein in the step, b) the *Aristotela chilensis* callus is maintained in a photoperiod of between 12 to 20 light hours and between 12 to 4 hours of the darkness per day, with a light intensity of between 5,000 to 20,000 lux.

6. The process according to claim 1, wherein additionally at the end of the step b), the anthocyanins are extracted from the *Aristotela chilensis* callus.

7. The process according to claim 1, wherein at the end of the step b), cells of *Aristotela chilensis* are dried and ground until obtaining an anthocyanins-enriched powder.

* * * * *